US008882809B2

(12) United States Patent
Walker et al.

(10) Patent No.: US 8,882,809 B2
(45) Date of Patent: Nov. 11, 2014

(54) PEDICLE SCREWS AND METHODS OF USING THE SAME

(75) Inventors: John Lawrence Walker, Madison, MS (US); James Milton Phillips, Star, MS (US); Justin Kyle Johnson, Brookhaven, MS (US); Gilbert Monroe Aust, Jr., Huntsville, AL (US)

(73) Assignee: Spinal USA, Inc., Parsippany, NJ (US)

( * ) Notice: Subject to any disclaimer, the term of this patent is extended or adjusted under 35 U.S.C. 154(b) by 0 days.

(21) Appl. No.: 13/571,723

(22) Filed: Aug. 10, 2012

(65) Prior Publication Data

US 2012/0303064 A1 Nov. 29, 2012

Related U.S. Application Data

(63) Continuation of application No. 12/510,897, filed on Jul. 28, 2009, now Pat. No. 8,241,341.

(60) Provisional application No. 61/162,113, filed on Mar. 20, 2009.

(51) Int. Cl.
*A61B 17/70* (2006.01)

(52) U.S. Cl.
CPC ......... *A61B 17/7037* (2013.01); *A61B 17/7035* (2013.01)
USPC ............................ 606/267; 606/266; 606/306

(58) Field of Classification Search
USPC .................................. 606/266, 267, 270, 306
See application file for complete search history.

(56) References Cited

U.S. PATENT DOCUMENTS

| 2,346,346 A | 4/1944 | Anderson |
| 4,907,926 A | 3/1990 | Wing |
| 4,946,458 A | 8/1990 | Harms et al. |
| 5,092,867 A | 3/1992 | Harms et al. |
| 5,196,013 A | 3/1993 | Harms et al. |
| 5,207,678 A | 5/1993 | Harms et al. |
| 5,443,467 A | 8/1995 | Biedermann et al. |
| 5,466,237 A | 11/1995 | Byrd, III et al. |
| 5,474,551 A | 12/1995 | Finn et al. |
| 5,474,555 A | 12/1995 | Puno et al. |
| 5,520,690 A | 5/1996 | Errico et al. |

(Continued)

FOREIGN PATENT DOCUMENTS

| WO | WO 97/02786 | 1/1997 |
| WO | WO 98/52482 | 11/1998 |
| WO | WO 2008/024373 | 2/2008 |

OTHER PUBLICATIONS

International Search Report and Written Opinion dated May 17, 2010 for PCT Application No. PCT/US2010/028016 filed on Mar. 19, 2010.

(Continued)

*Primary Examiner* — Andrew Yang
(74) *Attorney, Agent, or Firm* — Knobbe, Martens, Olson & Bear, LLP.

(57) ABSTRACT

Pedicle screws that can include a pedicle screw body, housing, plurality of clamps, rod, and set screw are disclosed herein. The clamps may be positioned side by side inside the lower portion of the housing. When the rod and set screw are provided in the housing, the set screw applies a force on the rod and the rod engages the plurality of clamps, causing the clamps to frictionally engage a head of the pedicle screw between the clamps.

19 Claims, 6 Drawing Sheets

(56) References Cited

U.S. PATENT DOCUMENTS

| | | |
|---|---|---|
| 5,531,746 A | 7/1996 | Errico et al. |
| 5,549,608 A | 8/1996 | Errico et al. |
| 5,554,157 A | 9/1996 | Errico et al. |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,607,426 A | 3/1997 | Ralph et al. |
| 5,609,593 A | 3/1997 | Errico et al. |
| 5,609,594 A | 3/1997 | Errico et al. |
| 5,628,740 A | 5/1997 | Mullane |
| 5,643,265 A | 7/1997 | Errico et al. |
| 5,647,873 A | 7/1997 | Errico et al. |
| 5,653,763 A | 8/1997 | Errico et al. |
| 5,667,507 A | 9/1997 | Corin et al. |
| 5,667,508 A | 9/1997 | Errico et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,392 A | 11/1997 | Richelsoph et al. |
| 5,688,273 A | 11/1997 | Errico et al. |
| 5,688,274 A | 11/1997 | Errico et al. |
| 5,690,630 A | 11/1997 | Errico et al. |
| 5,709,684 A | 1/1998 | Errico et al. |
| 5,716,356 A | 2/1998 | Biedermann et al. |
| 5,725,588 A | 3/1998 | Errico et al. |
| 5,728,098 A | 3/1998 | Sherman et al. |
| 5,733,285 A | 3/1998 | Errico et al. |
| 5,752,955 A | 5/1998 | Errico |
| 5,797,911 A | 8/1998 | Sherman et al. |
| 5,800,435 A | 9/1998 | Errico et al. |
| 5,810,818 A | 9/1998 | Errico et al. |
| 5,810,819 A | 9/1998 | Errico et al. |
| 5,817,094 A | 10/1998 | Errico et al. |
| 5,863,293 A | 1/1999 | Richelsoph |
| 5,876,402 A | 3/1999 | Errico et al. |
| 5,879,350 A | 3/1999 | Sherman et al. |
| 5,882,350 A | 3/1999 | Ralph et al. |
| 5,885,284 A | 3/1999 | Errico et al. |
| 5,885,286 A | 3/1999 | Sherman et al. |
| 5,888,204 A | 3/1999 | Ralph et al. |
| 5,891,145 A | 4/1999 | Morrison et al. |
| 5,904,683 A | 5/1999 | Pohndorf et al. |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,090,111 A | 7/2000 | Nichols |
| 6,113,601 A | 9/2000 | Tatar |
| 6,132,432 A | 10/2000 | Richelsoph |
| 6,132,434 A | 10/2000 | Sherman et al. |
| 6,146,383 A | 11/2000 | Studer et al. |
| 6,187,005 B1 | 2/2001 | Brace et al. |
| 6,248,105 B1 | 6/2001 | Schlapfer et al. |
| 6,254,602 B1 | 7/2001 | Justis |
| 6,261,287 B1 | 7/2001 | Metz-Stavenhagen |
| 6,280,442 B1 | 8/2001 | Barker et al. |
| 6,287,311 B1 | 9/2001 | Sherman et al. |
| 6,290,703 B1 | 9/2001 | Ganem |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,454,768 B1 | 9/2002 | Jackson |
| 6,454,773 B1 | 9/2002 | Sherman et al. |
| 6,471,705 B1 | 10/2002 | Biedermann et al. |
| 6,482,207 B1 | 11/2002 | Errico |
| 6,485,491 B1 | 11/2002 | Farris et al. |
| 6,485,494 B1 | 11/2002 | Haider |
| 6,488,681 B2 | 12/2002 | Martin et al. |
| 6,530,929 B1 | 3/2003 | Justis et al. |
| 6,537,276 B2 | 3/2003 | Metz-Stavenhagen |
| 6,540,748 B2 | 4/2003 | Lombardo |
| 6,558,387 B2 | 5/2003 | Errico et al. |
| 6,565,565 B1 | 5/2003 | Yuan et al. |
| 6,565,567 B1 | 5/2003 | Haider |
| 6,582,436 B2 | 6/2003 | Schlapfer et al. |
| 6,585,740 B2 | 7/2003 | Schlapfer et al. |
| 6,660,004 B2 | 12/2003 | Barker et al. |
| 6,666,867 B2 | 12/2003 | Ralph et al. |
| 6,689,133 B2 | 2/2004 | Morrison et al. |
| 6,726,687 B2 | 4/2004 | Jackson |
| 6,733,502 B2 | 5/2004 | Altarac et al. |
| 6,764,515 B2 | 7/2004 | Ralph et al. |
| 6,780,186 B2 | 8/2004 | Errico et al. |
| 6,858,030 B2 | 2/2005 | Martin et al. |
| 6,905,500 B2 | 6/2005 | Jeon et al. |
| 6,945,972 B2 | 9/2005 | Frigg et al. |
| 7,008,422 B2 | 3/2006 | Foley et al. |
| 7,022,122 B2 | 4/2006 | Amrein et al. |
| RE39,089 E | 5/2006 | Ralph et al. |
| 7,128,743 B2 | 10/2006 | Metz-Stavenhagen |
| 7,141,051 B2 | 11/2006 | Janowski et al. |
| 7,875,065 B2 | 1/2011 | Jackson |
| 2004/0024464 A1 | 2/2004 | Errico et al. |
| 2005/0033436 A1 | 2/2005 | Schlapfer et al. |
| 2005/0228382 A1 | 10/2005 | Richelsoph et al. |
| 2005/0251141 A1 | 11/2005 | Frigg et al. |
| 2006/0074419 A1 | 4/2006 | Taylor et al. |
| 2006/0084979 A1 | 4/2006 | Jackson |
| 2006/0084980 A1 | 4/2006 | Melkent et al. |
| 2006/0084996 A1 | 4/2006 | Metz-Stavenhagen |
| 2006/0149240 A1 | 7/2006 | Jackson |
| 2006/0149244 A1 | 7/2006 | Amrein et al. |
| 2006/0247631 A1 | 11/2006 | Ahn et al. |
| 2006/0271047 A1 | 11/2006 | Jackson |
| 2007/0049933 A1 | 3/2007 | Ahn et al. |
| 2007/0270813 A1 | 11/2007 | Garamszegi |
| 2008/0004625 A1 | 1/2008 | Runco et al. |
| 2008/0015580 A1* | 1/2008 | Chao ............................ 606/61 |
| 2008/0161853 A1 | 7/2008 | Arnold et al. |
| 2008/0188898 A1 | 8/2008 | Jackson |
| 2008/0269809 A1 | 10/2008 | Garamszegi |

OTHER PUBLICATIONS

Search Report and Opinion for European Application No. 10754190.6 filed Mar. 19, 2010 mailed Nov. 29, 2013.

\* cited by examiner

PEDICLE SCREWS AND METHODS OF USING THE SAME

CROSS-REFERENCE TO RELATED APPLICATIONS

This application is a continuation of U.S. patent application Ser. No. 12/510,897, filed on Jul. 28, 2009, which claims the priority benefit under 35 U.S.C. §119(e) of U.S. Provisional Application Ser. No. 61/162,113, filed on Mar. 20, 2009, each of which is incorporated herein by reference in its entirety for all purposes.

BACKGROUND

1. Field of the Invention

Disclosed herein are pedicle screws related to the field of orthopedic surgery. More particularly, certain embodiments disclosed herein relate to a pedicle screw and methods of use.

2. Description of the Related Art

Spinal fusion encompasses a surgical technique in which two or more vertebrae are connected together. This technique may be used for multiple indications, including abnormal spinal curvature (e.g., scoliosis) and weakening or injuring of the vertebrae or spinal disc.

In some instances, this process is accomplished and/or supplemented using a plurality of screws implanted into the pedicle of adjacent vertebrae and joined together by a series of one or more rods. The pedicle screw may have an enlarged head that interfaces with a housing having a corresponding cavity, thus allowing for a range of polyaxial articulation between the screw and the housing. After the pedicle screw is implanted into bone, a rod may be placed in the housing, and a set screw may delivered into engagement with the housing, applying a downward force on the rod to hold the assembly together. This downward force is also supposed to cause engagement of the head of the pedicle screw relative to the housing, to thereby fix the position of the pedicle screw relative to the housing and prevent disengagement. However, prior pedicle screw designs may not provide sufficient force to hold the pedicle screw relative to the housing to fix their relative locations and/or prevent disengagement.

SUMMARY

Described herein are pedicle screws that can include a screw body, a plurality of clamps, a housing, and a set screw. Methods of assembling and implanting the pedicle screws described herein are also included. These pedicle screws and related methods are described in greater detail below.

Some embodiments herein are directed to a pedicle screw that can include a threaded screw body having a proximal end and a distal end, the proximal end including an at least partially ball-shaped member; a housing having an upper portion with an upper opening and a lower portion with a lower opening extending along a first axis of the housing, the upper portion being internally threaded and the lower portion having a curved internal surface, and a third opening and a fourth opening along a second axis transverse to the first axis adapted to receive an elongated rod; a plurality of clamps positioned side-by-side adjacent the lower portion of the housing, each of the clamps having an upper portion with a cylindrical outer surface and a lower portion with a curved outer surface and a ball-shaped inner surface, the curved outer surface of the lower portion adapted to engage the curved internal surface of the lower portion of the housing, the upper portion of the clamps adapted to contact the elongated rod, and the ball-shaped inner surface adapted to engage the ball-shaped member; and a set screw configured to be received within the internally threaded first portion of the housing, wherein the set screw when engaged in the first portion applies a force onto the rod when received in the housing, the rod engaging the plurality of clamps to frictionally engage the ball-shaped member against the ball-shaped inner surface of each of the clamps.

In some embodiments, the ball-shaped inner surface includes a plurality of grooves. In some embodiments, the diameter of the ball-shaped member is less than the inner diameter of the lower opening of the housing. In some embodiments, the pedicle screw includes no more than two clamps. In some embodiments, each clamp has an upper portion with an indentation shaped to receive the rod. In some embodiments, the pedicle screw further includes a crimp from the outside of the housing to hold the clamps within the housing. In some embodiments, the radius of curvature of the curved outer surface of the lower portion of each of the clamps is different from the radius of curvature of the curved internal surface of the lower portion of the housing.

Some embodiments herein are directed to a pedicle screw that can include a threaded screw body having a proximal end and a distal end, the proximal end including an enlarged head; a housing having an upper portion having an upper opening and a lower portion having a lower opening extending along a first axis of the housing, the upper portion being internally threaded and the lower portion having a gradually decreasing dimension toward the lower opening, and a third opening and a fourth opening along a second axis transverse to the first axis adapted to receive an elongated rod; a plurality of clamps positioned side-by-side adjacent the lower portion of the housing, each of the clamps having an upper surface adapted to engage the elongated rod and a lower surface adapted to engage the enlarged head; and a set screw configured to be received within the internally threaded first portion, wherein the set screw when engaged in the first opening applies a force onto the rod when received in the housing, the rod engaging the plurality of clamps and causing the clamps to frictionally engage the enlarged head between the lower surfaces of the clamps.

Some embodiments herein are directed to a pedicle screw that can include a threaded screw body having a proximal end and a distal end, the proximal end including an at least partially ball-shaped member; a housing having an upper portion with an upper opening and a lower portion with a lower opening extending along a first axis of the housing, the upper portion being internally threaded and the lower portion having an internal surface, and a third opening and a fourth opening along a second axis transverse to the first axis adapted to receive an elongated rod; a plurality of clamps positioned side-by-side adjacent the lower portion of the housing, each of the clamps having an upper portion and a lower portion, the lower portion having an outer surface and a ball-shaped inner surface, the outer surface of the lower portion adapted to engage the internal surface of the lower portion of the housing, the upper portion of the clamps adapted to contact the elongated rod, and the ball-shaped inner surface adapted to engage the ball-shaped member; and a set screw configured to be received within the internally threaded first portion of the housing, wherein the set screw when engaged in the first portion applies a force onto the rod when received in the housing, the rod engaging the plurality of clamps to frictionally engage the ball-shaped member against the ball-shaped inner surface of each of the clamps.

DETAILED DESCRIPTION

Figure 1:
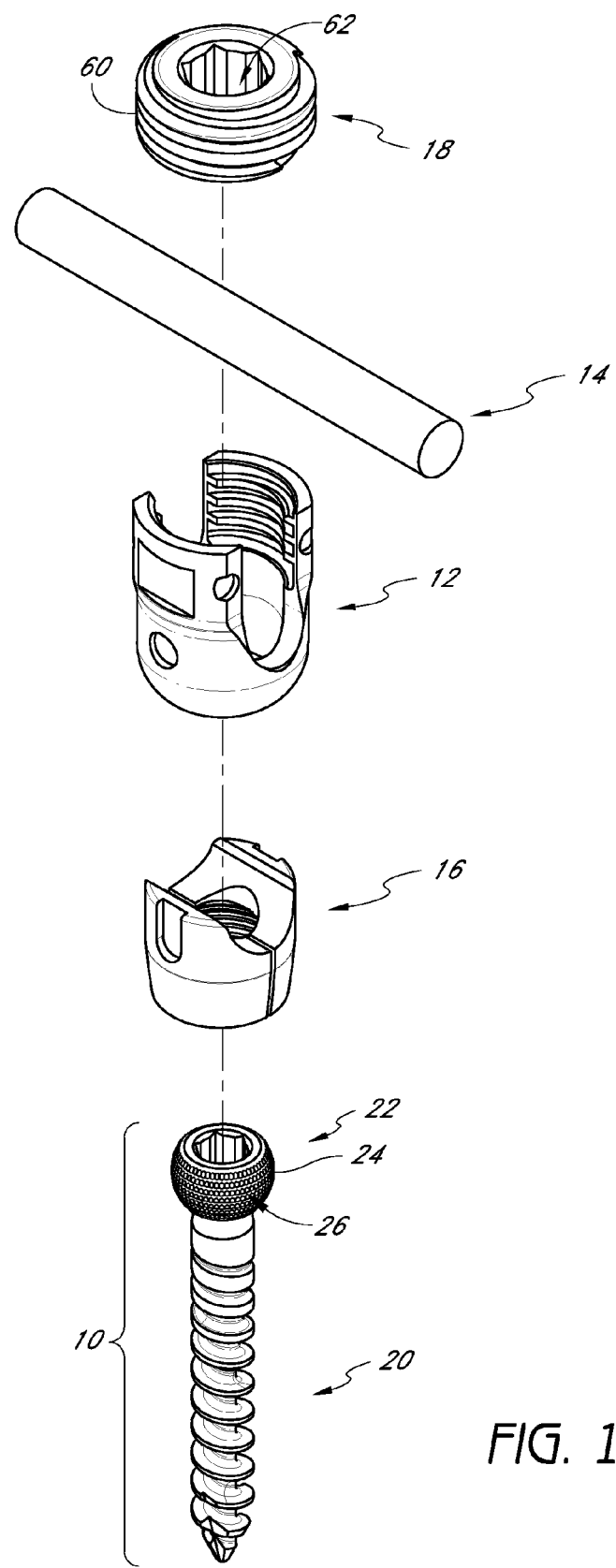
FIG. 1 is an exploded view of an embodiment of a pedicle screw disclosed herein.

As illustrated in FIG. 1, embodiments disclosed herein are directed to a pedicle screw which can include a screw body 10, a housing 12, a rod 14, a plurality of clamps 16, and a set screw 18. In some embodiments, one or more of these components may be constructed from a metal, such as titanium or alloys thereof. For example, one or more components may include titanium 6AL 4V ELI.

As shown in FIG. 1, in some embodiments, the rod 14 may be approximately straight. In other embodiments, the rod 14 may be curved. The rod 14 may be of various lengths and diameters, for example, to span two or more adjacent vertebrae. Those of ordinary skill in the art may appreciate that any rod commonly used in spinal implantation may be used with the pedicle screw disclosed herein.

The pedicle screw disclosed herein may include a set screw 18, as shown in FIG. 1. In some embodiments, the set screw 18 may have external threading 60 as illustrated in FIG. 1 so as to be configured to be received by an internally threaded housing 12 as described below, though a set screw may also be provided having internal threading to correspond with an externally threaded housing. The set screw 18 may have square threads, though other types of threads are also contemplated. In some embodiments, the set screw 18 has an inner recess 62 which may be approximately hexagonally-shaped. The inner recess 62 may be shaped and adapted to receive a torque wrench.

Figure 2:
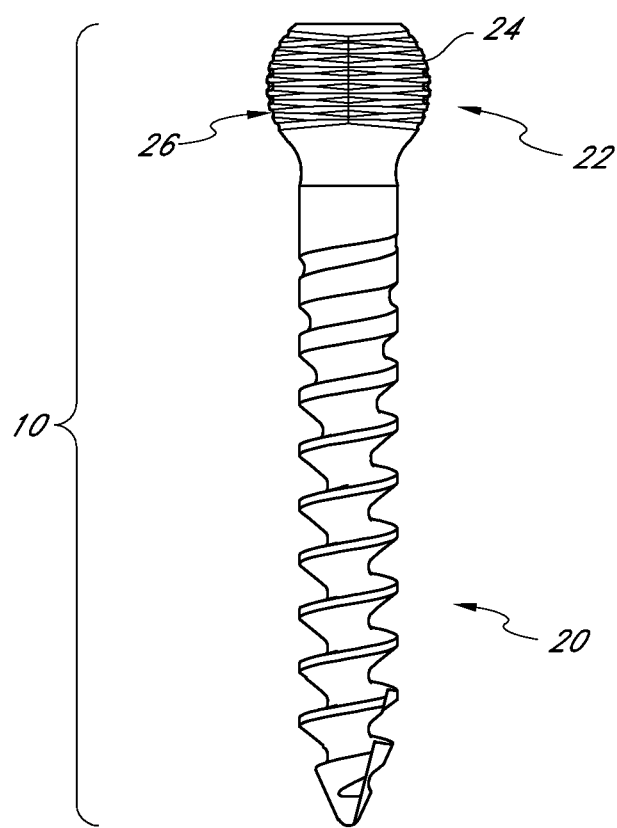
FIG. 2 is a side view of a screw body as disclosed herein.

FIG. 2 illustrates a side view of a screw body 10 as described herein. The screw body 10 may have a proximal end 22 and a distal end 20. As shown in FIG. 2, the distal end 20 may be at least partially threaded. In some embodiments, the distal end 20 of the screw body 10 may be adapted for implantation into the spine of a patient. For example, the distal end 20 of the screw body 10 can be adapted for implantation into the pedicle portion of a patient's vertebrae. As shown in FIG. 2, the proximal end 22 may include an enlarged head 24. In some embodiments, the enlarged head 24 may be approximately spherical, e.g., ball-shaped. The enlarged head 24 may have a roughened surface 26. As illustrated in FIG. 2, the roughened surface 26 may include threading, such as in the shape of a criss-cross pattern. In another embodiment, the threads may be parallel to each other. In other embodiments, the roughened surface 26 may include a sandblasted surface or the roughened surface 26 may be grooved. Those of ordinary skill in the art will appreciate that various other roughened surfaces may be used. In other embodiments, the enlarged head 24 may have an approximately smooth surface (not shown).

Figure 3:
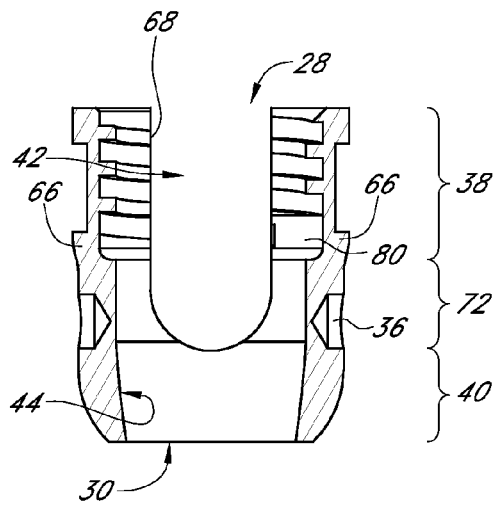
FIG. 3 is a cross-sectional view of an embodiment of a housing of a pedicle screw disclosed herein.
Figure 4:
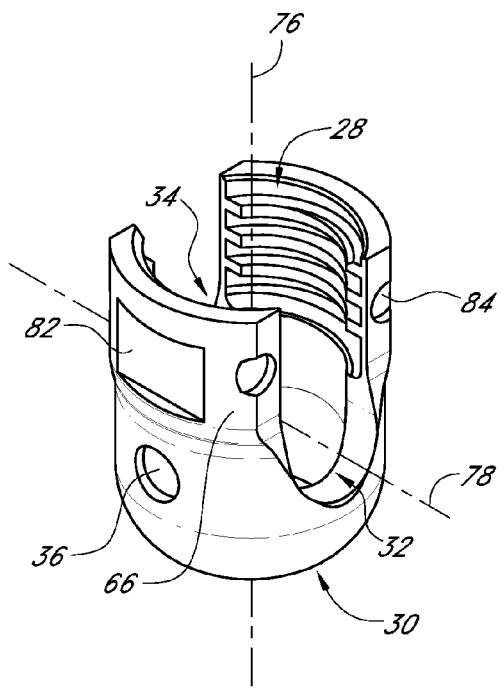
FIG. 4 is a side view of an embodiment of a housing of a pedicle screw disclosed herein.

The pedicle screw disclosed herein may also include a housing 12, shown in FIGS. 3-4. The housing 12 may include an upper portion 38 having an upper opening 28 and a lower portion 40 having a lower opening 30. In some embodiments, both the upper opening 28 and the lower opening 30 may extend along a first axis 76 of the housing 12. The upper opening 28 and the lower opening 30 may be connected so as to create a through hole passing from the upper portion 38 through the lower portion 40. The diameter of the upper opening 28 may be larger than the diameter of the enlarged head 24 of the screw body 10 so that the screw can pass into the housing through the upper opening 28. In some embodiments, the diameter of the lower opening 30 may be larger than the diameter of the enlarged head 24 of the screw body 10. In other words, the diameter of the enlarged head 24 may be smaller than that of the lower opening 30 of the housing 12. Thus, the screw body 10 may be loaded into the housing 12 from either the upper opening 28 or the lower opening 30. In an embodiment, the screw body 10 may be loaded into the housing 12 from the upper opening 28. As shown in FIG. 4, the housing 12 may also include a third opening 32 and a fourth opening 34, both extending along a second axis 78 of the housing 12 which is transverse to the first axis, and intersecting with an upper edge of the housing 12. In some embodiments, the third opening 32 and the fourth opening 34 can be adapted to receive the rod 14, with the width of the openings being about the same or slightly larger than the diameter of the rod. In an embodiment, both the third opening 32 and the fourth opening 34 can be approximately "U"-shaped, though other shapes, such as an "O"-shape, may also be used.

As shown in FIG. 3, the upper portion 38 may define an interior recess 42 surrounded by two approximately partially cylindrically-shaped walls 66, with the openings 32 and 34 extending between the walls. The outer surface of the walls 66 may be adapted to couple to one or more insertion tools. As shown in FIG. 4, each wall 66 may have one or more circular indentations 84 adapted to couple to a side hook holder. Each wall 66 may also have a rectangular indentation 82 adapted to couple to an insertion tool, such as an alignment tube, rod fork, and persuader, and/or a tightening tool such as an anti-torque wrench.

At least part of the walls surrounding the interior recess 42 of the upper portion 38 may be internally threaded. In the embodiment illustrated, the threading 68 starts at the top of the housing 12, and terminates above the bottom of the third and fourth openings 32, 34. In some embodiments, the threading 68 may not extend beyond a point at or below the rod 14 when it is resting in the housing 12 upon one or more clamps 16, described below. An undercut region 80 may be provided below the threading 68. The internal threading may be adapted to receive and engage the set screw 18.

The housing 12 may have an intermediate portion 72 starting below the undercut region 80. As illustrated in FIG. 3, the inner wall of the intermediate portion 72 may be substantially cylindrical in shape, with the openings 32 and 34 extending into the intermediate portion. Below the intermediate portion 72 there may be a lower portion 40. The lower portion 40 may have a gradually decreasing diameter towards the bottom of the housing 12 along an interior surface 44. As shown in FIG. 3, the interior surface 44 of the lower portion 40 may be curved. In an embodiment, the curved interior surface 44 may be non-spherical. In other words, the curved interior surface 44 may have a center of radius that differs from its center of rotation. In other embodiments, the interior surface 44 of the lower portion 40 may be approximately conical.

Figure 5:
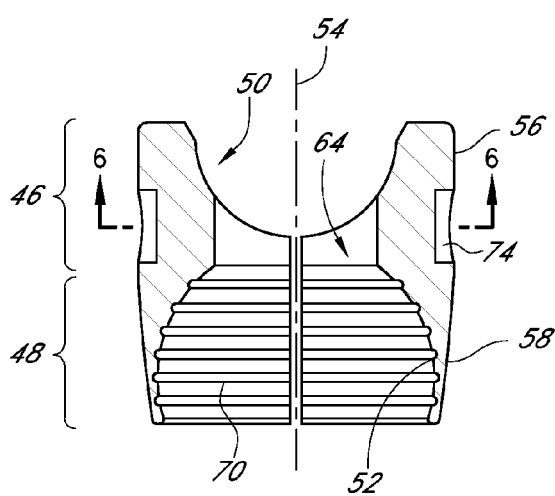
FIG. 5 is a cross-sectional view of a pair of clamps as disclosed herein.
Figure 6:
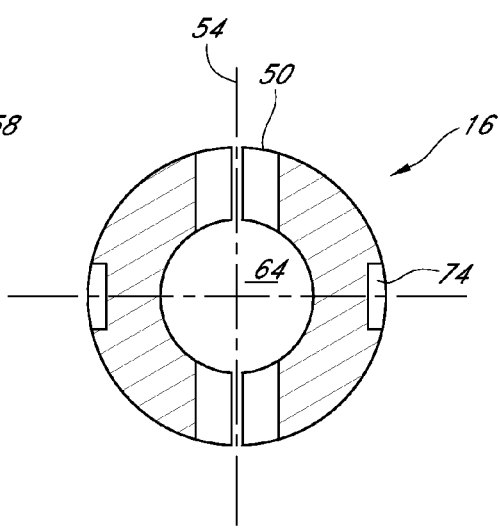
FIG. 6 is a cross-sectional view of the pair of clamps of FIG. 5, taken through line 6-6.

The pedicle screw described herein may have a plurality of clamps 16. In some embodiments, the pedicle screw described herein may have two clamps 16 placed side-byside, for example, as shown in FIGS. 5 and 6. Although the pedicle screw disclosed herein may be primarily described as having two clamps 16, those of ordinary skill will appreciate that additional clamps 16 may also be used. For example, in another embodiment, the pedicle screw may have four side-by-side clamps 16.

As shown in FIG. 5, each clamp 16 may have an upper portion 46 and a lower portion 48. In the illustrated embodiment, the upper portion 46 may have an indentation 50 adapted for receiving the rod 14, the indentation 50 being shaped approximately as a portion of a cylinder. In an embodiment with two clamps 16, for example as shown in FIG. 5, each indentation 50 may cooperate with each other to receive the rod 14. The indentation 50 may be on a top surface of the upper portion 46. In other embodiments, the indentation 50 may be on a side surface of the upper portion 46. As illustrated, the clamps 16 can be symmetrical. In other embodiments, the clamps 16 can be asymmetrical. FIG. 5 shows an embodiment where the clamps 16 can be placed next to each other horizontally. There may be a plane 54 defined by the interface between each clamp 16 that completely separates each ball clamp. In an embodiment with two clamps 16, each indentation 50 may be adapted to receive the rod 14 such that the rod 14 is oriented parallel to the plane 54, as shown in FIG. 5. In another embodiment with two clamps 16, each indentation 50 may be adapted to receive the rod 14 such that the rod 14 is perpendicular to the plane 54 (not shown). One or more embodiments described herein may cause increased frictional engagement between the rod 14 and the clamps 16, resulting in a pedicle screw with overall increased locking capability and integrity.

As shown in FIG. 5, the lower portion 48 of each clamp 16 may have an inner surface 52. In some embodiments, the inner surface 52 may be shaped as a concave approximately spherical, or ball-shaped, segment. As shown in FIG. 5, each inner surface 52 may cooperate with each other to form a cavity 70, which may be approximately spherical or ball-shaped. The horizontal cross section of the cavity 70 may increase from the top of the cavity towards the middle, and may decrease from the middle to the bottom of the cavity. The decreased cross section at the bottom of the cavity 70 may contribute to the engagement between the clamps 16 and the enlarged head 24 of the screw body 10. The radius of the inner surface 52 may be larger than the radius of the enlarged head 24 of the screw body 10. In other embodiments, the radius of the inner surface 52 may be approximately the same as or smaller than the radius of the enlarged head 24 of the screw body 10. The inner surface 52 can be adapted to engage the enlarged head 24 of the screw body 10. In some embodiments, the inner surface 52 may be roughened. In an embodiment, the inner surface 52 may be threaded. In another embodiment, the inner surface 52 may be sandblasted (not shown). In yet another embodiment, the inner surface 52 may include a plurality of grooves, as illustrated in FIG. 5. Those of ordinary skill in the art will appreciate that various other roughened surfaces may be used. In other embodiments, the inner surface 52 may be substantially smooth.

When assembled, a passageway 64 may extend from the collective upper portions 46 of each clamp 16 to the collective lower portions 48, as shown in FIG. 5. In some embodiments, the passageway 64 may provide access to the enlarged head 24 of the screw body 10 for implantation into a patient's vertebrae. In these embodiments, the passageway 64 may be used for driving the screw into the vertebrae when the screw has already been placed between the clamps 16 and within the housing 12.

Each ball clamp 16 has upper and lower outer surfaces 56, 58. The upper and lower outer surfaces 56, 58 of each clamp 16 may have a horizontal cross section that is approximately partly circular. For example, in an embodiment with two clamps 16, the upper and lower outer surfaces 56, 58 of each clamp 16 may have a horizontal cross section that is approximately a half-circle, as shown in FIG. 6. The outer surface 56 of the upper portion 46 may be approximately partially cylindrical in shape. In some embodiments, an exterior radius of the upper portion 46 is smaller than an interior radius of the upper portion 38 of the housing 12. The exterior radius of the upper portion 46 may also be smaller than the inner wall of the intermediate portion 72 of the housing 12. In some embodiments, the upper portion 46 may also include one or more indentations 74. The indentation 74 may be adapted to receive a crimp 36, described further below. In some embodiments, each clamp 16 may have one indentation 74. When arranged in the housing 12, the indentations may be aligned opposite each other, as depicted in FIG. 5.

In some embodiments, as illustrated in FIG. 5, the outer surface 58 of the lower portion 48 gradually decreases in dimension towards the bottom of the clamp 16. As shown in FIG. 5, the outer surface 58 of the lower portion 48 in one embodiment may be curved. In an embodiment, the outer surface 58 of the lower portion 48 may be non-spherical. In other words, the outer surface 58 of the lower portion 48 may have a center of radius that differs from its center of rotation. In other embodiments, the outer surface 58 of the lower portion 48 may be approximately partially conical in shape.

Figure 7:
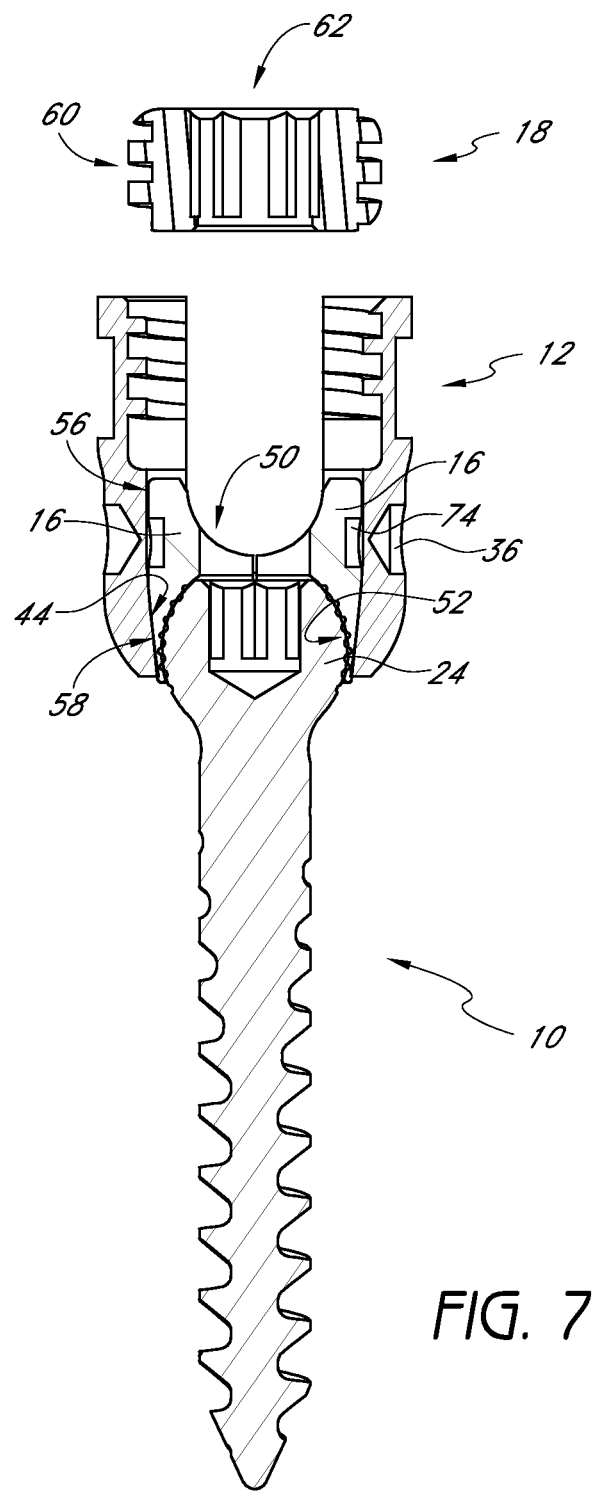
FIG. 7 is a cross-sectional view of an embodiment of a pedicle screw disclosed herein.

A cross-sectional view of an embodiment of a pedicle screw as partially assembled is shown in FIG. 7. The enlarged head 24 of the screw body 10 may be adapted to fit at least partially within the inner surface 52 of each clamp 16. The clamps 16 may fit within the interior surface 44 of the lower portion 40 of the housing 12. In some embodiments, the radius of curvature of the outer surface 58 of the lower portion 48 of the clamp 16 may be different from the radius of curvature of the interior surface 44 of the lower portion 40 of the housing 12. Advantageously, this difference in radii may allow for variation in the loading point between the clamps 16 and the housing 12. For example, where the outer surface 58 of the lower portion 48 of the clamps 16 has a radius of curvature that is smaller than that of the interior surface 44 of the lower portion 40 of the housing 12, the result may be a loading point that is localized relatively close to the enlarged head 24 of the screw body 10. In the alternate, the outer surface 58 of the lower portion 48 of the clamp 16 may have a radius of curvature that is equal to that of the interior surface 44 of the lower portion 40 of the housing 12. Advantageously, these embodiments may result in a greater surface area of contact between the clamp 16 and the housing 12, thus resulting in increased stability. In some embodiments, the clamps 16 may contact each other upon placement into the interior surface 44 of the lower portion 40 of the housing 12. In other embodiments, the clamps 16 may not contact each other. In these embodiments, the clamps 16 may be separated by plane 54, as shown in FIG. 5.

The screw body 10, clamps 16, and housing 12 may be preassembled. The screw body 10 and the clamps 16 may be inserted into either the upper opening 28 or the lower opening 30 of the housing 12. In an embodiment, the clamps 16 may be loaded into the upper opening 28 of the housing 12 and the screw body 10 may be loaded into the lower opening 30 of the housing 12. In another embodiment, the clamps 16 can be placed on the enlarged head 24 of the screw body 10, and together they can be loaded into the upper opening 28 of the housing 12. When assembled, one or more clamps 16 may extend to a depth below the housing 12. In the embodiment illustrated in FIG. 7, when the pedicle screw is assembled, the enlarged head 24 does not contact the inner surface 44 of the lower portion 40 of the housing 12, and the enlarged head has a smaller diameter than the smallest inner diameter of the inner surface 44. While in this position, the screw body 10 may be capable of polyaxial movement relative to the clamps 16 and/or housing 12.

The indentation 50 on each clamp 16 may be aligned with the third and fourth openings 32, 34 of the housing 12 to accommodate rod 14. In this manner, the rod may be positioned substantially parallel to the plane 54. After inserting each ball clamp into position inside the housing, each clamp 16 may be held in place within the housing 12 and/or aligned via an engagement member, such as crimp 36 made from the outside of the housing 12 in the intermediate portion 72. The crimp 36 may be formed by applying force to a selected portion of the housing 12 via a press and punch apparatus, and may engage the indentations 74 on the sides of the clamps 16. In some embodiments, each clamp 16 may be capable of at least a limited range of motion with crimp 36 in place.

Figure 8:
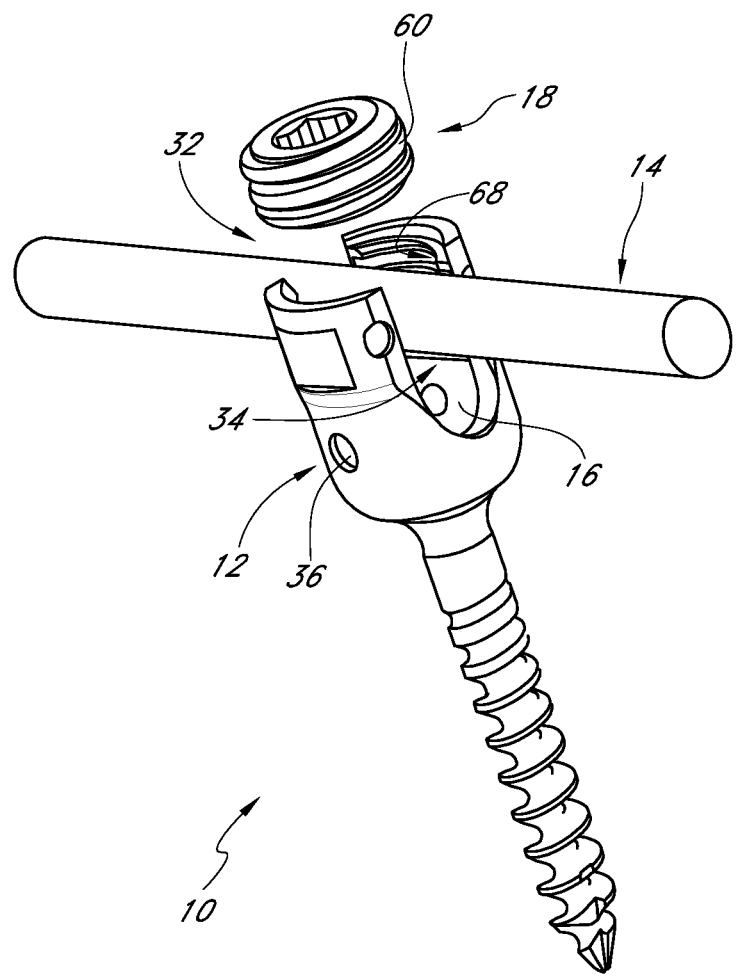
FIG. 8 is a perspective view of an embodiment of a pedicle screw disclosed herein.

With the clamps 16 and pedicle screw 10 held in position in the lower portion of the housing, the rod 14 may be inserted into the third and fourth openings 32, 34 of the housing 12 and may be adapted to rest upon one or more clamps 16, as shown in FIG. 8. In some embodiments, the threading on the interior recess 42 may not extend beyond a point at or below the rod 14 when it is resting upon one or more clamps 16. Upon insertion, the rod 14 may be oriented approximately perpendicular to the screw body 10. In the illustrated embodiment, the rod 14 does not directly contact the enlarged head 24 of the screw body 10.

The external threading 60 of the set screw 18 may be adapted to mate with the internal threading of the interior recess 42 of the upper portion 38 of the housing 12. As the set screw 18 is threaded into the housing 12, the set screw 18 may contact and apply force to rod 14. The rod 14 may consequently engage the clamps 16, applying downward pressure thereto. The outer surface 58 of the lower portion 48 of each clamp 16 may then engage the interior surface 44 of the lower portion 40 of the housing 12. In some embodiments, the radii of both the outer surface 58 and the inner surface 44 decrease towards the lower portions of each clamp 16 and housing 12, respectively. In these embodiments, as the clamps 16 are pushed down into the housing 12, the inner surface 44 of the housing 12 may apply force to one or more outer surfaces 56, 58 of each clamp 16. Consequently, the inner surface 52 of each clamp 16 may frictionally engage the enlarged head 24 of the screw body 10. In some embodiments, the frictional engagement between each clamp 16 and the enlarged head 24 may be augmented via a roughened surface on the clamp 16 and/or the enlarged head 24. As each clamp 16 increases frictional engagement with the enlarged head 24, polyaxial movement of the screw body 10 may be reduced, thus holding the screw body in place at a particular orientation.

Figure 9:
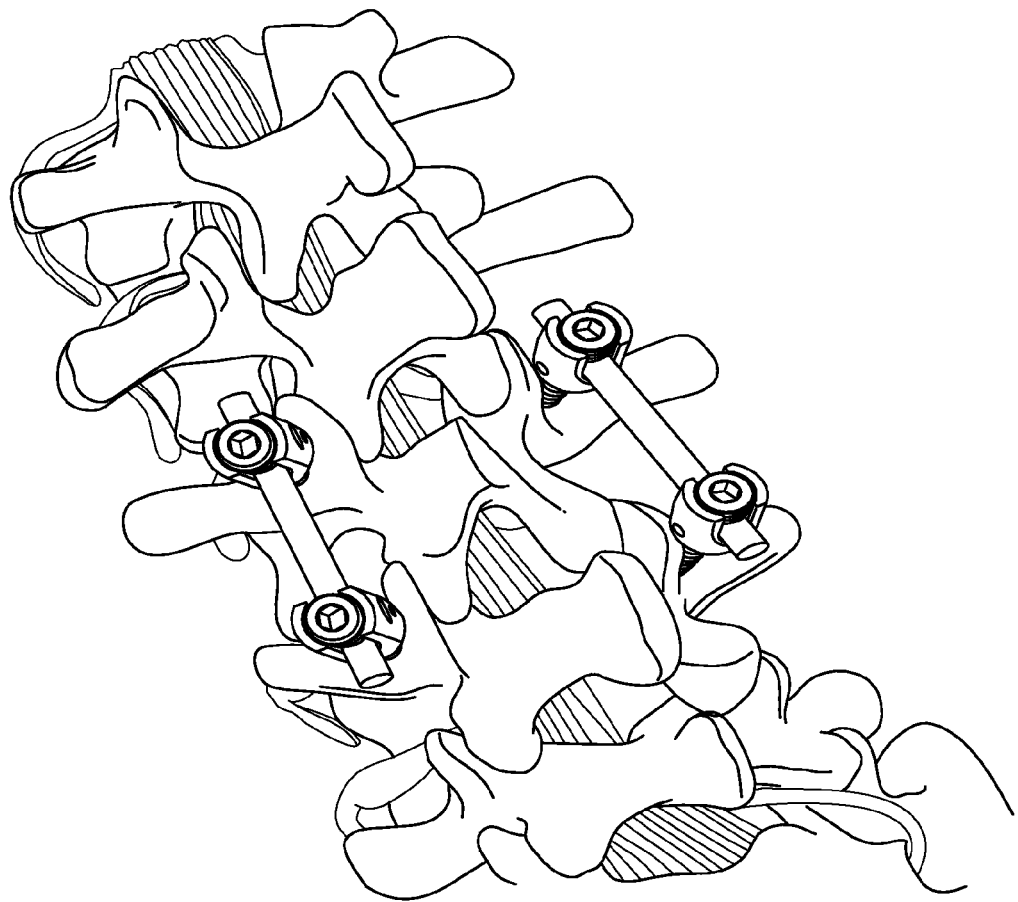
FIG. 9 illustrates a pedicle screw disclosed herein implanted in a patient.

As shown in FIG. 9, the pedicle screw disclosed herein may be implanted in the vertebrae of a patient. In some embodiments the pedicle screw may be implanted in the patient's thoracolumbar spine. In some embodiments, the distal end 20 of the screw body 10 may be adapted for implantation into a pedicle of the patient's vertebrae. Prior to implantation, a pathway for receiving the distal end 20 of the screw body 10 may be created in the pedicle using methods known to those skilled in the art. In some embodiments, a preassembled combination of the screw body 10, clamps 16, and housing 12 may be inserted into the pathway. As mentioned previously, the enlarged head 24 of the screw body 10 may be accessed via the passageway 64 between the clamps 16. The insertion tools may be adapted to correspond to the dimensions of the enlarged head 24 of the screw body 10. In some embodiments, a polyaxial screwdriver may be used to insert the distal end 20 of the screw body 10 into the pathway. After insertion, the rod 14 may be placed into the third and fourth openings 32, 34 using a rod holder. The set screw 18 may then be threaded into the housing 12 and secured to lock the housing 12 and the rod 14 in place at a chosen orientation. Various methods may be used to insert and secure the set screw 18, as may be appreciated by those of ordinary skill in the art. For example, various insertion tools may be used, including but not limited to an alignment tube, a rod fork, and a persuader. In some embodiments, the set screw 18 may be tightened using an anti-torque wrench and a torque wrench. Advantageously, one or more of the features described herein may contribute to an increased locking strength. Those of ordinary skill in the art may appreciate that a plurality of screw bodies 10 may be coupled to a single rod 14, and that multiple screw bodies 10 and rods 14 may be implanted in a patient.

The various pedicle screws and methods described above provide a number of ways to carry out some preferred embodiments of the invention. Of course, it is to be understood that not necessarily all objectives or advantages described may be achieved in accordance with any particular embodiment described herein. Thus, for example, those skilled in the art will recognize that the compositions may be made and the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various components, features and steps discussed above, as well as other known equivalents for each such component, feature or step, can be mixed and matched by one of ordinary skill in this art to make compounds and perform methods in accordance with principles described herein.

Although the invention has been disclosed in the context of some embodiments and examples, it will be understood by those skilled in the art that the invention extends beyond these specifically disclosed embodiments to other alternative embodiments and/or uses and obvious modifications and equivalents thereof. Accordingly, the invention is not intended to be limited by the specific disclosures of preferred embodiments herein.

What is claimed is:

1. A pedicle screw comprising:

a threaded screw body having a proximal end and a distal end, the proximal end comprising an enlarged head;

a housing having an upper portion with an upper opening and a lower portion with a lower opening extending along a first axis of the housing, the upper portion being internally threaded and an internal surface of the lower portion curving toward the lower opening, and a third opening and a fourth opening along a second axis transverse to the first axis adapted to receive an elongated rod;

one or more clamps positioned adjacent the lower portion of the housing and having an upper portion with a cylindrical outer surface and a lower portion with a curved outer surface, the curved outer surface of the lower portion adapted to engage the curved internal surface of the lower portion of the housing, the upper portion of the one or more clamps adapted to contact the elongated rod, and an inner surface of the lower portion of the one or more clamps adapted to engage the enlarged head, wherein a radius of curvature of the curved outer surface of the lower portion of the one or more clamps is different from a radius of curvature of the curved internal surface of the lower portion of the housing; and a set screw configured to be received within the internally threaded first portion of the housing, wherein the set screw when engaged in the first portion applies a force onto the rod when received in the housing, the rod engaging the one or more clamps to frictionally engage the enlarged head against the inner surface of the one or more clamps.

2. The pedicle screw of claim 1, wherein the inner surface of the lower portion of the one or more clamps comprises a plurality of grooves.

3. The pedicle screw of claim 2, wherein the plurality of grooves are aligned horizontally on the inner surface.

4. The pedicle screw of claim 1, wherein an outer dimension of the enlarged head is less than an inner dimension of the lower opening of the housing.

5. The pedicle screw of claim 1, comprising no more than two clamps.

6. The pedicle screw of claim 1, wherein the one or more clamps have an upper portion with an indentation shaped to receive the rod.

7. The pedicle screw of claim 1, further comprising a crimp from an outside of the housing to hold the one or more clamps within the housing.

8. The pedicle screw of claim 1, wherein the radius of curvature of the curved outer surface of the lower portion of the one or more clamps is less than the radius of curvature of the curved internal surface of the lower portion of the housing.

9. The pedicle screw of claim 1, wherein the radius of curvature of the curved outer surface of the lower portion of the one or more clamps is greater than the radius of curvature of the curved internal surface of the lower portion of the housing.

10. A pedicle screw comprising:
a threaded screw body having a proximal end and a distal end, the proximal end comprising an enlarged head;
a housing having an upper portion having an upper opening and a lower portion having a lower opening extending along a first axis of the housing, the upper portion being internally threaded and the lower portion having a gradually decreasing dimension toward the lower opening, and a third opening and a fourth opening along a second axis transverse to the first axis adapted to receive an elongated rod;
two clamps completely separated from each other by a plane and positioned in the housing and having an upper surface adapted to engage the elongated rod such that the rod is oriented parallel to the plane and a lower surface adapted to engage the enlarged head, wherein the plane is parallel to the second axis of the housing; and
a set screw configured to be received within the internally threaded first portion, wherein the set screw when engaged in the first opening applies a force onto the rod when received in the housing, the rod engaging the clamps and causing the clamps to frictionally engage the enlarged head.

11. The pedicle screw of claim 10, wherein the lower surface of the one or more clamps adapted to engage the enlarged head comprises a plurality of grooves aligned horizontally on the lower surface.

12. The pedicle screw of claim 10, wherein the enlarged head comprises a roughened surface.

13. The pedicle screw of claim 10, wherein the one or more clamps have an upper portion with a cylindrical outer surface and a lower portion with a curved outer surface.

14. The pedicle screw of claim 12, wherein an outer dimension of the lower portion is less than or about equal to an outer dimension of the upper portion.

15. The pedicle screw of claim 12, wherein an outer dimension of the lower portion gradually decreases toward a lower end of the lower portion.

16. The pedicle screw of claim 10, each clamp further comprising an indentation configured to receive a crimp extending from an outside of the housing into engagement with the indentation to hold the clamp in the housing, wherein an axis extending from one indentation to the other is perpendicular to the plane separating the two clamps.

17. A pedicle screw comprising:
a threaded screw body having a proximal end and a distal end, the proximal end comprising an enlarged head;
a housing having an upper portion with an upper opening and a lower portion with a lower opening extending along a first axis of the housing, the upper portion being internally threaded and the lower portion having an internal surface, and a third opening and a fourth opening along a second axis transverse to the first axis adapted to receive an elongated rod;
two clamps completely separated from each other by a plane and positioned in the housing and having an upper portion and a lower portion, the upper portion of the clamps adapted to contact the elongated rod such that the rod is oriented parallel to the plane, and an inner surface of the lower portion of the clamps adapted to engage the enlarged head, wherein the plane is parallel to the second axis of the housing, and wherein the inner surface of the lower portion of one or more clamps comprises a plurality of horizontally-aligned grooves; and
a set screw configured to be received within the internally threaded first portion of the housing, wherein the set screw when engaged in the first portion applies a force onto the rod when received in the housing, the rod engaging the clamps to frictionally engage the enlarged head against the inner surface of the one or more clamps.

18. The pedicle screw of claim 17, wherein the upper portion of the one or more clamps has a cylindrical outer surface and the outer surface of the lower portion is curved, the upper portion cylindrical outer surface gradually transitioning to the curved outer surface of the lower portion.

19. The pedicle screw of claim 17, further comprising a crimp from an outside of the housing to hold the one or more clamps within the housing.

* * * * *